United States Patent [19]

Oxenrider

[11] Patent Number: 4,551,519

[45] **Date of Patent: * Nov. 5, 1985**

[54] PROCESS FOR THE PRODUCTION OF FLUORINATED PYROMELLITATE CONTAINING MIXTURES USEFUL AS SURFACTANTS

[75] Inventor: Bryce C. Oxenrider, Florham Park, N.J.

[73] Assignee: Allied Corporation, Morris Township, Morris County, N.J.

[ * ] Notice: The portion of the term of this patent subsequent to Nov. 8, 2000 has been disclaimed.

[21] Appl. No.: 490,593

[22] Filed: May 2, 1983

[51] Int. Cl.[4] ........................ C08G 63/12; C07C 67/08

[52] U.S. Cl. .................................... 528/296; 428/378; 528/366; 560/87

[58] Field of Search ................... 528/296, 366; 560/87

[56] References Cited

U.S. PATENT DOCUMENTS 4,321,403 3/1982 Oxenrider ............................ 560/87

4,414,277 11/1983 Oxenrider .......................... 428/395

*Primary Examiner*—Christopher A. Henderson

*Attorney, Agent, or Firm*—Richard C. Stewart, II; Gerhard H. Fuchs

[57] ABSTRACT

A novel process is disclosed for producing fluorinated pyromellitate surfactants. The process comprises two primary steps. The first step involves reacting pyromellitic dianhydride with fluorinated alcohol at a mole ratio of about two moles of fluorinated alcohol per mole of pyromellitic dianhydride, thereby producing a pyromellitate having two fluorinated esters moieties and two carboxylic acid moieties. Thereafter, the fluorinated pyromellitate with carboxylic acid moieties is reacted with an oxirane compound in the presence of trimellitic anhydride to produce fluorinated pyromellitate mixtures having a reduced percentage of fluorine.

18 Claims, No Drawings

PROCESS FOR THE PRODUCTION OF FLUORINATED PYROMELLITATE CONTAINING MIXTURES USEFUL AS SURFACTANTS

BACKGROUND OF THE INVENTION

The present invention relates to a process for the production of highly effective surface treating agents. The surface treating agents produced in accordance with this invention comprise mixtures containing fluorinated pyromellitate nuclei. The pyromellitate nuclei contain fluorinated ester moieties which impart water and oil repelling characteristics to various fibers.

U.S. Pat. No. 4,209,610 (Mares et al., 1980) discloses fluorinated pyromellitates useful as surface modifiers for polyamides and polyesters. One preferred group of compounds in that patent are those of the formula:

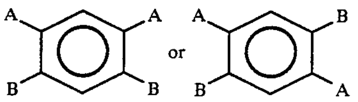

wherein A is a fluorinated ester such as $CF_3(CF_2)_pR'O(O)C—$ and wherein B is $HOCH(CH_2Cl)CH_2O(O)C—$; wherein R′ is ethylene and p is a mixture of integers such as 3, 5, 7, 9 and 11 for different chains. Such products are formed by the reaction of pyromellitic dianhydride with a fluorinated alcohol, and then the reaction of the product diacid/diester with epichlorohydrin. Specifically, the product is produced by reaction of two moles of fluorinated alcohol with each mole of pyromellitic dianhydride to form the diacid/diester. Each mole of the diacid/diester is then reacted with two moles of epichlorohydrin to produce the product. Because the oxirane may react at the one or two carbon, the product will normally contain minor amounts of material with B being $HOCH_2CH(CH_2Cl)O(O)C—$ (the product with a pendant primary alcohol) as well as major amounts of material with B being $HOCH(CH_2Cl)CH_2O(O)C—$ (the product with a pendant secondary alcohol). Other patents relating to the production of this product include U.S. Pat. No. 4,252,982 (Oxenrider 1981) wherein an ester solvent is used and U.S. Pat. No. 4,321,403 (Oxenrider et al., 1981) wherein N-methylpyrrolidone is used as solvent. Methods for applying the compound in aqueous emulsions to fibers are disclosed in U.S. Pat. Nos. 4,192,754 (Marshall et al., 1980), 4,134,839 (Marshall, 1979), 4,190,545 (Marshall et al., 1980), 4,193,880 (1980), 4,283,292 (Marshall, 1981) and 4,317,736 (Marshall, 1982).

My copending, commonly assigned application Ser. No. 380,188, now U.S. Pat. No. 4,446,306, describes a process for the production of pyromellitate oligomers useful as surface treating agents wherein a mole ratio of fluorinated alcohol to pyromellitic dianhydride of less than 2:1 is employed.

In a modification of copending, commonly assigned application Ser. No. 380,188, application Ser. No. 412,620, now U.S. Pat. No. 4,414,277, describes a simple two step process for the production of oligomeric surfactants. Initially, pyromellitic dianhydride is reacted with fluorinated alcohol with the mole ratio of pyromellitic dianhydride to fluorinated alcohol being about 2:1. Thereafter, the fluorinated pyromellitate compound is reacted with an oxirane compound in the presence of additional pyromellitic dianhydride to produce oligomeric mixtures.

The fluorinated pyromellitate containing mixtures of the present invention have extremely high resistance to soiling, and the soil resistant properties imparted to fibers by the compositions of this invention are retained by the fibers after numerous laundering cycles. Therefore, fibers treated with the fluorinated pyromellitate containing mixtures of the present invention will retain soil resistance properties for long periods of time in an environment where they are ultimately employed. Furthermore, as described in each of the above patents, an annealing step is employed after the application of the compound to the fiber. It is desirable to be able to lower the temperature of the annealing step, for energy savings, without impairing either the initial soil resistance or the retention of soil resistance after laundering. With the fluorinated pyromellitate containing mixtures of the present invention, the annealing step may be accomplished at temperatures as low as about 50° C.

Also, some of the fluorinated surfactants of the present invention contain a lesser mole percent of fluorine than most of the compositions described by the above-referenced patents or pending patent applications. Since fluorinated alcohol from which the fluorine moiety is derived is somewhat expensive, any reduction in the amount of fluorinated alcohol that must be employed to produce a given amount of product results in a cost savings.

BRIEF DESCRIPTION OF THE INVENTION

The present invention relates to novel organic fluorinated pyromellitate mixtures useful for the modification of surface properties and to a process for the production of the novel mixtures. Accordingly, the process of this invention comprises:

(a) reacting pyromellitic dianhydride with fluorinated alcohol at a mole ratio of about two moles of fluorinated alcohol per mole of pyromellitic dianhydride to produce a pyromellitate having two fluorinated ester moieties and two carboxylic acid moieties;

(b) reacting said pyromellitate of step (a) with an oxirane compound selected from the group consisting of epichlorohydrin, epibromohydrin, and propylene oxide in the presence of trimellitic anhydride to produce said organic fluorinated pyromellitate containing mixtures.

The oxirane compound reacts with said carboxylic acid moieties of said pyromellitate and with the carboxylic acid moiety of said trimellitic anhydride to produce an ester having a primary or secondary alcohol, and wherein said primary or secondary alcohol of said ester moiety of said pyromellitate reacts with the anhydride moiety of said trimellitic anhydride to produce an ester-linking moiety and an additional carboxylic acid moiety capable of reacting with said oxirane compound to produce additional esters having primary or secondary alcohols.

The present invention further includes polyamide and polyester fibers having applied thereto the fluorinated pyromellitate containing mixtures described above. Finally, the present invention includes a process of applying the mixtures of fibers, with preferred annealing conditions for such process being between about 80° C. and about 120° C., although temperatures between about 50° C. and about 150° C. may be used.

DETAILED DESCRIPTION OF THE INVENTION

The process of the present invention employs four reactants. Pyromellitic dianhydride is one of the four reactants. Preferably, commercial grade pyromellitic dianhydride of greater than 98% purity should be employed for the practice of the present invention. Common impurities which can be tolerated in minor amounts include pyromellitic monoanhydride.

A second reactant is a fluroinated alcohol. While any alcohol having a relatively long chain of $CF_2$ groups with a terminal $CF_3$ group may be employed, the preferred fluorinated alcohols can be represented by the formula $CF_3(CF_2)_pR'OH$, wherein R' is alkylene of 2-6 carbons, and p is an integer between 3 and 15, preferably between 3 and 13. In that formula R' is preferably ethylene, 1,2-propylene or 1,4-butylene, and is most preferably ethylene. It is contemplated, and in fact preferred, to use a mixture of alcohols, particularly mixtures with the same R' group such as ethylene, but with varying values for p. A representative commercial mixture of fluorinated alkyl ethanols has the formula $CF_3CF_2(CF_2CF_2)_nCH_2CH_2OH$ wherein n is 2-4 with lesser amounts of n being 1 and 5, and traces of n being 6 or 7.

A third reactant used in the present process is preferably epichlorohydrin. It may also be the corresponding bromo compound, known as epibromohydrin or propylene oxide. It will be appreciated that all three of these compounds are three carbon oxiranes with the third carbon being of the formula $CH_2X$ wherein X is Cl, Br or H. Trimellitic anhydride is the fourth reactant.

The process of this invention may be conducted in any of the organic solvents utilized in forming the compounds of *Mares et al., Oxenrider et al.,* or *Oxenrider.* Illustrative examples of useful solvents incltde dimethylformamide, N-methylpyrrolidone and aliphatic esters having a boiling point below about 150° C., such as methyl acetate, ethyl acetate, propyl acetate, etc. Other suitable solvents include aliphatic ketones such as methyl isobutyl ketone. The preferred solvent for the practice of this invention is N-methylpyrrolidone.

The order of reaction for the process of this invention is to initially react the fluorinated alcohol with pyromellitic dianhydride to produce a pyromellitate intermediate having two fluorinated ester moieties and two free acid moieties. The ratio of the reactants employed in the production of the diester/diacid intermediate should be about two moles of fluorinated alcohol per mole of pyromellitic dianhydride. This initial reaction may be conducted at temperatures between about 20° C. and about 80° C. with about 45° C. being the preferred temperature for this step of the process. The length of this initial reaction will range from about 2 hours to about 40 hours depending upon the reaction temperature and whether a catalyst such as triethylamine is employed. Higher reaction temperatures and catalysts will enhance the rate of the reaction and consequently, reduce the time required for the reaction to occur. The diester/diacid intermediate produced via the reaction of a mole ratio of fluorinated alcohol to pyromellitic dianhydride of 2:1 is the same intermediate produced in the above *Mares et al., Oxenrider et al.,* and *Oxenrider* patents. This intermediate is also produced by the first step of the process described by copending application Ser. No. 412,620, now U.S. Pat. No. 4,414,277. The described first step of the process of this invention may be illustrated by reaction (1) as follows:

(1)

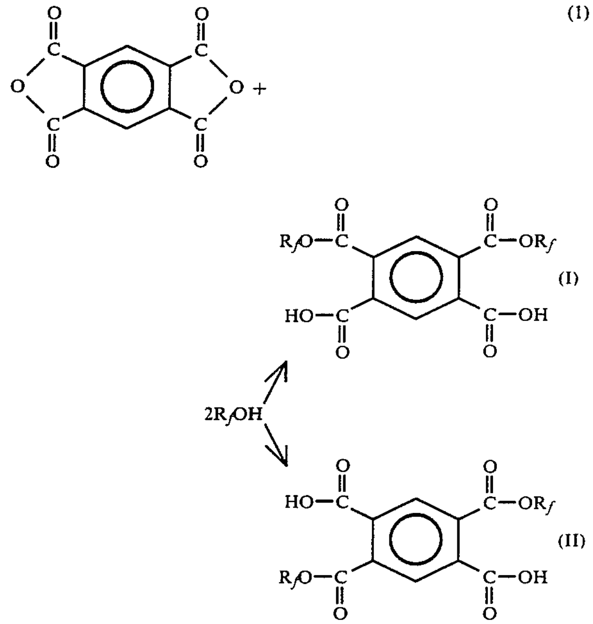

(I)

(II)

wherein $R_fOH$ is a fluorinated alcohol as described hereinbefore.

The diester/diacids represented by structures (I) and (II) above depict the meta and para isomers. It should be appreciated that the diester/diacid intermediate will actually constitute a mixture of the meta and para isomers. It is not necessary to isolate the diester/diacid before proceeding to the next step or steps of this invention. However, the diester/diacid could be isolated if it was desired to do so.

Following production of the diester/diacid intermediate, an excess of the third reactant, an oxirane compound as described above, is added to the reaction medium. The excess of oxirane employed will be more than 2 moles of oxirane compound per mole of pyromellitic dianhydride utilized in the first step of the process. As will become apparent, the amount of excess of oxirane compound employed will depend somewhat upon the amount of trimellitic anhydride added to the reaction medium in a later step. The oxirane compound will react with the free acid moieties of the diester/diacid intermediate to produce a pyromellitate tetraester having two fluorinated ester moieties and two ester moieties having a primary or secondary alcohol. Production of the ester moiety having a primary or secondary alcohol results from the reaction of the oxirane compound at the 1 or 2 carbon with a free acid group. For example, reaction (2) below illustrates the reaction between epichlorohydrin and one isomer of the diester/-diacid intermediate.

(2)

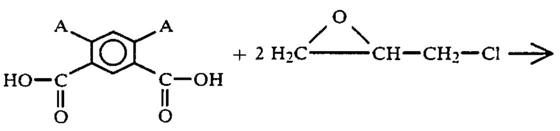

-continued

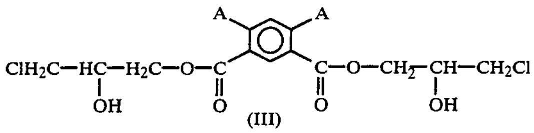

(III)

In reaction (2), A is a fluorinated ester moiety as previously described. In structure (III), the ester group containing the alcohol will now be referred to as B. Therefore, structure (III) may be illustrated as follows:

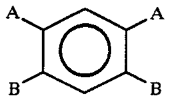

(IV)

As previously, stated, the para isomer of the diester/diacid intermediate is also formed. Therefore, structure (III) may also take the following form:

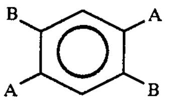

(V)

100° C. with about 55° C. to about 75° C. being the preferred temperature for this step of the invention.

The temperature for the second step will be that necessary to achieve the desired level of conversion (as measured by the disappearance of free carboxyl groups), such desired level being discussed below. Representative times for the second step are about 4 to about 20 hours, which may overlap with the third step as discussed below.

Reaction (2) above, the second step of the process, should preferably be conducted in the presence of a catalyst. Suitable catalysts include triethylamine, tributylamine, lutidine, pyridine and the like with triethylamine being the preferred catalyst for utilization in the process of this invention.

The next reaction necessary for the practice of the process of this invention involves the reaction of a B group primary or secondary alcohol of structure IV or V with an anhydride moiety of trimetallic anhydride. Reaction between said alcohol moieties and said anhydride moieties produces an ester linking group and a free acid group. This reaction, reaction (3), may be illustrated as follows by the reaction of a pyromellitate tetraester produced in accordance with this invention with two molecules of trimetallitic anhydride:

(3)

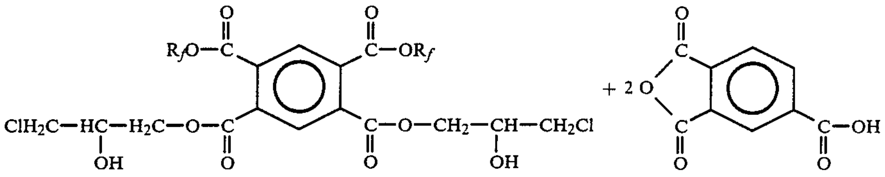

1 2

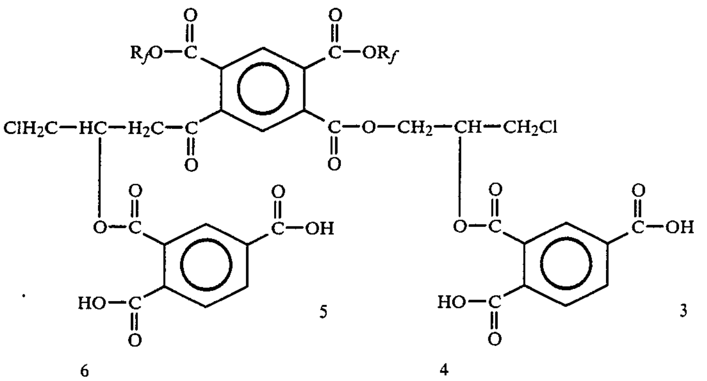

VI

It should also be appreciated that if the oxirane compound reacts at the number 2 carbon, the B group will take the form of

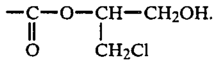

However, B groups having a primary alcohol are believed to represent only about 10% of the total number of B groups which are formed.

The reaction between the diester/diacid intermediate and the oxirane compound, reaction (2), should be conducted at a temperature between about 20° C. and about In order for reaction (3) to occur, trimellitic anhydride must be present in the reaction medium after the formation of the diester/diacid in reaction (1). The trimellitic dianhydride may be added to the reaction medium simultaneously with the addition of the oxirane compound. When this procedure is followed, as soon as free acid groups are esterified by the oxirane compound thereby forming B groups containing a primary or secondary alcohol, the alcohol may react with an anhydride moiety in accordance with reaction (3) as described. It is especially preferred, however, to monitor reaction (2) by the disappearance of carboxyl groups via standard titration techniques and to add trimellitic anhydride to the reaction medium when about 50% to about 100% of the free acids have been esterified. It is especially preferred to add trimellitic anhydride to the reaction mixture when about 85% to 100% of the carboxyl groups have been esterified as determined by tritration procedures.

As described, once trimellitic anhydride is added to the reaction medium, reaction (3) of the process of this invention will occur if ester groups having a primary or secondary alcohol (B groups) are present. Reaction (3) will occur at temperatures between about 20° C. and about 100° C. with about 55° C. to about 75° C. being the preferred temperature for reaction (3). The time required to complete reaction (3) will range from about 1 hour to about 3 hours, depending upon the reaction temperature, amount of trimellitic anhydride employed, etc. Reaction (3) produces an ester linking group, L, having the following structure:

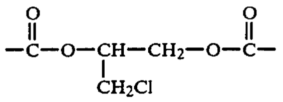

It should be appreciated that chlorine in the above structure could alternately be bromine or hydrogen if epibromohydrin or propylene oxide were to be employed in place of epichlorohydrin.

Examination of structure VI reveals that structure VI has four free acid groups (3, 4, 5, and 6 as labeled) which are capable of undergoing a further reaction. Free acid groups 3, 4, 5, and 6 are capable of reacting with oxirane compound to form additional B groups having the B group structure previously described (i.e. ester groups having a primary or secondary alcohol). The organic structure formed by the reaction of the free acid groups of structure VI is the trimer represented by structure VII as follows:

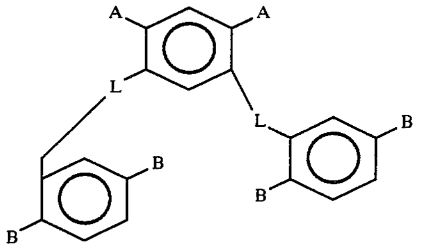

VII

It will be appreciated that the esterification of free acid groups 3 and 5 will begin to occur as soon as trimellitic anhydride is added to the reaction medium. These groups are, of course, present as free acid groups on the trimellitic anhydride molecule. However, free acid groups 4 and 6 will not be present initially. They are formed when hydroxyls 1 and 2 of structure VI of the pyromellitate tetraester depicted in reaction (3) react with the anhydride moiety of trimellitic anhydride thereby producing the described linking groups and free acid groups 4 and 6.

It will be appreciated that structure VII represents one isomer that may be produced by the process of this invention. Other isomers may occur, of course, depending upon whether the metal or para pyromellitate isomer is involved and upon where the secondary hydroxyl of the pyromellitate attacks the anhydride moiety of trimellitic anhydride.

For illustrative purposes, structures VIII through XI below represent compositions which may be formed by the process of this invention. Structures VIII through XI are intended to illustrate, but not to exhaust, the components of the novel fluorinated pyromellitate containing mixtures that may be produced by the process of this invention produced by the process of this invention.

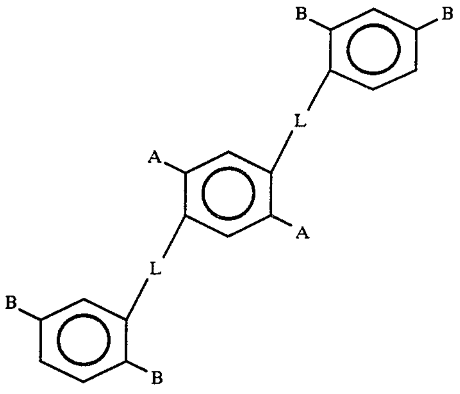

VIII

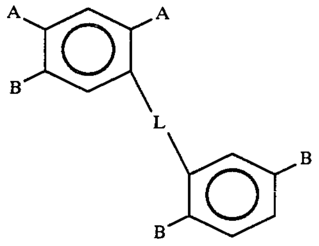

IX

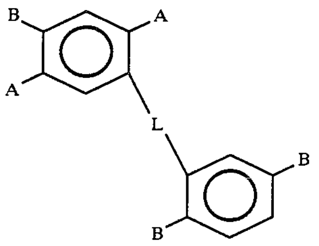

X

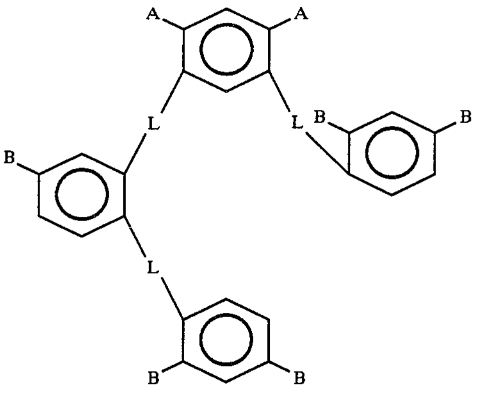

XI

In structures VIII through XI, A represents a fluorinated ester group as previously described; B represents an ester group having a primary or secondary alcohol as previously described; and L represents an ester linking group as previously described.

The fluorinated pyromellitate containing mixtures of this invention will comprise a mixture of compounds of the type illustrated by structures VII-XI in addition to the other similar structures. The exact composition of the mixtures is not predictable. However, to some extent the composition of the mixtures will be influenced by the molar ratio of pyromellitic dianhydride to trimellitic anhydride. The mole ratio of pyromellitic dianhydride to trimellitic anhydride that may be employed in the practice of this invention may range from about 10:1 to about 1:3. Preferably, however, the molar ratio of pyromellitic dianhydride to trimellitic anhydride will range from about 5:1 to about 1:2. When less than two moles of trimellitic anhydride per mole of pyromellitic dianhydride are employed, it is likely that a number of isomers of the type represented by structures IX and X will be present in the final product mixture. This is because there won't be enough trimellitic anhydride molecules for all the B group alcohols of the pyromellitic tetraesters to react with. Also, in cases of this nature, the final product mixture will likely contain a certain amount of pyromellitate tetraesters as represented by structures IV and V. On the other hand, when at least two moles of trimellitic anhydride are employed for each mole of pyromellitic dianhydride, the final product mixture will likely contain a greater number of isomers of the type represented by structures VII and VIII.

It is desirable to conduct the process of this invention in a dry atmosphere. Pressure is not critical, with atmospheric pressure being suitable. Solvent amounts are not critical, with sufficient solvent being enough to keep at least half of the pyromellitates and fluoroalcohols in solution (since precipitate can redissolve into solution as it reacts), and preferably all of the reactants, intermediates, and products in solution.

Once formed, the fluorinated pyromellitate containing mixtures of the present invention are normally recovered from the solvent in a manner analogous to that employed in the above *Mares et al., Oxenrider et al.* and *Oxenrider* patents. Thus, for example, the entire reaction mixture may be added to a non-solvent such as water when N-methylpyrrolidone is used as solvent, or a volatile ester or ketone solvent may be distilled from the reaction mixture. In either case, it is preferred to wash the initial product at least once with water in order to remove any remaining solvent and/or catalyst and/or unreacted reactants, and especially unreacted oxirane compound.

The product may then be applied to a polyamide or polyester fiber from an organic solvent such as acetone, methanol or dioxane. It is believed that the product mixtures can be applied to fibers in an emulsion similar to the emulsion described in U.S. Pat. No. 4,192,754 *Marshall et al.*, or in other emulsion systems such as those described in the other *Marshall* and *Marshall et al.* patents listed above. It is also believed that the compound may further be applied to the fiber along with other fiber treating agents, and especially spin finishes used to reduce friction of the fiber during processing.

Suitable fibers include poly(caproamide) (nylon 6), poly(hexamethyl diamine adipate) (nylon 6,6) and other polyamides of both the poly(amino acid) type and poly(diamine dicarboxylate) types such as poly(hexamethylene diamine sebacate) known as nylon 6,12. Also suitable are polyesters such as poly(ethylene terephthalate) (PET). Levels of application are not critical, with levels on a fluoride/fiber basis similar to the above patents being suitable (e.g. 0.05 to 0.25% fluoride).

Subsequent to fiber application, it is preferred that the treated fiber be annealed to improve the adherence of the treating agent to the fiber. Annealing temperatures for many surfactants such as those described in the Background section of this application are preferrably between about 100° C. and about 155° C. The present products have an annealing temperature range from about 50° C. to about 150° C. In many preferred embodiments of this invention, the annealing step is conducted at temperatures between about 80° C. and about 120° C.

EXAMPLES

In performing the reactions described by Examples 1–6, a 3-necked round bottom flask equipped with a stirring bar, thermometer, water condenser, nitrogen inlet and vent was employed. In each example, perfluoroalkylethanol refers to a mixture of fluorinated alcohols of the formula $CF_3CF_2(CF_2CF_2)_nCH_2CH_2OH$ with n being 2, 3, 4 or 5. The fluorinated alcohols contained 2.1 meq OH/g.

EXAMPLE 1

Di-(perfluoroalkylethyl)-bis-(3-chloro-2-hydroxypropyl)tetraester of pyromellitic dianhydride (22.5 g) was reacted with trimellitic anhydride (6.5 g, 33.85 meq) in N-methylpyrrolidone (35 mL) at 70° C. for 10 minutes. Epichlorohydrin (18.3 mL, 234.2 meq) and triethylamine (0.28 mL) was added to the reaction mixture and the reaction was continued for 9 hours at 70° C. Titration indicated that all carboxyl groups had reacted. The reaction mixture was cooled and poured into an ice-water bath with agitation to precipitate the product. Water was removed by decantation and the product was washed three more times in a similar manner. The product (25.7 g of a reddish-tan soft solid) was recovered by filtration and dried in a vacuum oven at room temperature. The structure of the product was confirmed by NMR.

EXAMPLE 2

Perfluoroalkylethanol (40.2 g, 84.4 meq), pyromellitic dianhydride (9.19 g, 84.4 meq) and N-methylpyrrolidone (43 mL) were added to a reaction flask to form a reaction mixture. The reaction mixture was heated to 45° C. and stirred for 18 hours in order to complete the initial reaction. The temperature of the reaction mixture was raised to 65° C. and epichlorohydrin (19.8 mL, 253.2 meq) and triethylamine (2.5 meq) were added to the reaction mixture. The reaction was continued for 4 additional hours. Tritration indicated the reaction was 97.8% complete. Trimellitic anhydride (16.21 g, 84.4 meq), epichlorohydrin (39.6 mL, 506.4 meq) and triethylamine (5 meq) were then added to the reaction mixture and the reaction was allowed to continue for 6.5 hours at 65° C. Titration indicated that all carboxyl groups had reacted. The product (65.9 g) was washed and recovered as in Example 1.

EXAMPLE 3

Perfluoroalkylethanol (55.7 g, 116.9 meq), pyromellitic dianhydride (12.7 g, 116.9 meq) and N-methylpyrrolidone (58 mL) were added to a reaction flask to form a reaction mixture. The reaction mixture was heated to 45° C. and stirred for 18 hours in order to complete the initial reaction. The temperature of the reaction mixture was raised to 65° C. and epichlorohydrin (27.4 mL, 350.7 meq) and triethylamine (3.5 meq) were added to the reaction mixture. The reaction was continued for 5 additional hours. Titration indicated that the reaction was complete. Trimellitic anhydride (19 g, 116.9 meq) was then added to the reaction mixture and the reaction was allowed to continue for 7 hours at 65° C. Titration indicated that all carboxyls had reacted. The product (93 g) was washed and recovered as in Example 1.

EXAMPLE 4

Perfluoroalkylethanol (80.1 g, 168.2 meq), pyromellitic dianhydride (18.3 g 168.2 meq) and N-methylpyrrolidone (81 mL) were added to a reaction flask to form a reaction mixture. The reaction mixture was heated to 45° C. and stirred for 23 hours in order to complete the initial reaction. Titration indicated the reaction was 97.2% complete. The temperature of the reaction mixture was raised to 65° C. and epichlorohydrin (39.4 mL, 504.6 meq) and triethylamine (5 meq) were added to the reaction mixture. The reaction was continued for 4.75 additional hours. Trimellitic anhydride (16.1 g, 84.1 meq) was then added to the reaction mixture and the reaction was allowed to continue for 8 hours at 65° C. Titration indicated that all carboxyl groups had reacted. The product (121.8 g) was washed and recovered as in Example 1.

EXAMPLE 5

Perfluoroalkylethanol (66.5 g, 139.65 meq), pyromellitic dianhydride (15.2 g, 139.65 meq) and N-methylpyrrolidone (67 mL) were added to a reaction flask to form a reaction mixture. The reaction mixture was heated to 45° C. and stirred for 18.5 hours in order to complete the initial reaction. The temperature of the reaction mixture was raised to 65° C. and epichlorohydrin (24.5 mL, 314.2 meq) and triethylamine (4.2 meq) were added to the reaction mixture. The reaction was continued for 5 additional hours. Titration indicated that the reaction was 91% complete. Trimellitic anhydride (6.7 g, 34.9 meq) was then added to the reaction mixture and the reaction was allowed to continue for 9 hours at 65° C. Titration indicated that the reaction was >98% complete. The product (84.8 g) was washed and recovered as in Example 1.

EXAMPLE 6

Perfluoroalkylethanol (71.6 g, 150.36 meq), pyromellitic dianhydride (16.4 g, 150.36 meq) and N-methylpyrrolidone (80 mL) were added to a reaction flask to form a reaction mixture. The reaction mixture was heated to 45° C. and stirred for 23 hours in order to complete the initial reaction. The temperature of the reaction mixture was raised to 65° C. and epichlorohydrin (14.1 mL, 180.44 meq) and triethylamine (4.5 meq) were added to the reaction mixture. The reaction was continued for 6.5 additional hours. Titration indicated the reaction was complete. The reaction mixture was stored in a refrigerator overnight. Thereafter, the reaction mixture was heated to 65° C. and trimellitic anhydride (2.89 g, 15.04 meq) was added and the reaction was continued for 7 hours at which time titration indicated that the reaction was 96.1% complete. Epichlorohydrin (7.02 mL, 90 meq) was added to the reaction mixture and the reaction was continued for 4 hours. Titration indicated that all carboxyl groups had reacted. The product (75.6 g) was washed and recovered as in Example 1.

EXAMPLE 7

PERFORMANCE EVALUATION

Solutions were prepared from the products of Examples 1-6 of 0.25 g of each product in 100 mL acetone. Swatches of nylon 6 tricot jersey fabric were dipped in the solutions, air dried for 1 to 3 hours and then annealed for 30 minutes in a circulating oven at selected temperatures. These nylon 6 swatches were then tested for oil repellency by the procedures of AATCC Test No 118-1966 initially and after being subjected to a number of laundry cycles. The results are displayed in Tables I to VI. In Table III, performance results are shown for a pyromellitate having a structure similar to the pyromellitates of *Mares et al., Oxenrider et al.* and *Oxenrider* and are employed in order to compare the oil repellency of the compositions of the present invention with the oil repellency of a pyromellitate that is presently being employed by the fiber industry as a surfactant. Thus, Table III contains an additional designation, comp., which illustrates the performance of the comparative material.

TABLE I

| | Anneal Temp. 70° C. Example | | | | | |
|---|---|---|---|---|---|---|
| Laundry Cycles | 1* | 2* | 3 | 4 | 5 | 6 |
| 0 | | | 6 | 6 | 6 | 7 |
| 1 | | | 6 | 6 | 6 | 7 |
| 2 | | | 6 | 6 | 6 | 7 |
| 3 | | | 6 | 6 | 6 | 5 |
| 4 | | | 6 | 5 | 5 | 5 |
| 5 | | | 5 | 5 | 5 | 3 |
| 6 | | | 3 | 4 | 4 | |
| 7 | | | | 4 | 3 | |
| 8 | | | | 3 | | |
| 9 | | | | | | |
| 10 | | | | | | |
| 11 | | | | | | |
| 12 | | | | | | |

*Nylon 6 swatches having the products of Examples 1 and 2 applied thereto were not annealed and tested at 70° C.

TABLE II

| | Anneal Temp. 80° C. Example | | | | | |
|---|---|---|---|---|---|---|
| Laundry Cycles | 1* | 2 | 3 | 4 | 5 | 6 |
| 0 | | 6 | 6 | 6 | 6 | 7 |
| 1 | | 6 | 6 | 6 | 6 | 7 |
| 2 | | 5 | 6 | 6 | 6 | 6 |
| 3 | | 5 | 6 | 6 | 6 | 6 |
| 4 | | 5 | 5 | 6 | 6 | 6 |
| 5 | | 4 | 5 | 6 | 6 | 5 |
| 6 | | 4 | 4 | 5 | 6 | 4 |
| 7 | | 4 | 4 | 5 | 6 | 3 |
| 8 | | 4 | 3 | 4 | 5 | |
| 9 | | 3 | | 3 | 4 | |
| 10 | | | | | 3 | |
| 11 | | | | | | |
| 12 | | | | | | |

*Nylon swatches having the product of Example 1 applied thereto were not annealed and tested at 80° C.

TABLE III

| | Anneal Temp. 90° C. Example | | | | | | |
|---|---|---|---|---|---|---|---|
| Laundry Cycles | 1 | 2 | 3 | 4 | 5 | 6 | Comp. |
| 0 | 7 | 6 | 6 | 6 | 6 | 7 | 7 |
| 1 | 6 | 6 | 6 | 6 | 6 | 7 | 4 |

TABLE III-continued

| | Anneal Temp. 90° C. Example | | | | | | |
|---|---|---|---|---|---|---|---|
| Laundry Cycles | 1 | 2 | 3 | 4 | 5 | 6 | Comp. |
| 2 | 6 | 5 | 6 | 6 | 6 | 6 | 3 |
| 3 | 6 | 5 | 6 | 6 | 6 | 6 | |
| 4 | 6 | 5 | 6 | 6 | 6 | 6 | |
| 5 | 5 | 4 | 5 | 6 | 6 | 6 | |
| 6 | 5 | 4 | 4 | 5 | 6 | 6 | |
| 7 | 5 | 4 | 4 | 5 | 6 | 4 | |
| 8 | 4 | 4 | 4 | 4 | 5 | 3 | |
| 9 | 4 | 4 | 3 | 3 | 4 | | |
| 10 | 4 | 3 | | | 4 | | |
| 11 | 3 | | | | 3 | | |
| 12 | | | | | | | |

TABLE IV

| | Anneal Temp. 100° C. Example | | | | | |
|---|---|---|---|---|---|---|
| Laundry Cycles | 1 | 2 | 3 | 4 | 5 | 6 |
| 0 | 6 | 6 | 6 | 6 | 6 | 7 |
| 1 | 6 | 6 | 6 | 6 | 6 | 7 |
| 2 | 6 | 6 | 6 | 6 | 6 | 6 |
| 3 | 5 | 5 | 6 | 6 | 6 | 6 |
| 4 | 5 | 5 | 5 | 6 | 6 | 6 |
| 5 | 5 | 5 | 5 | 6 | 6 | 6 |
| 6 | 5 | 4 | 4 | 5 | 6 | 5 |
| 7 | 5 | 4 | 4 | 5 | 6 | 5 |
| 8 | 4 | 4 | 3 | 5 | 5 | 4 |
| 9 | 4 | 3 | | 4 | 4 | |
| 10 | 3 | | | 3 | 4 | |
| 11 | | | | | 3 | |
| 12 | | | | | | |

TABLE V

| | Anneal Temp. 120° C. Example | | | | | |
|---|---|---|---|---|---|---|
| Laundry Cycles | 1 | 2 | 3 | 4 | 5 | 6 |
| 0 | 6 | 6 | 6 | 6 | 6 | 7 |
| 1 | 6 | 6 | 6 | 6 | 6 | 7 |
| 2 | 6 | 5 | 6 | 6 | 6 | 6 |
| 3 | 5 | 5 | 6 | 6 | 6 | 6 |
| 4 | 5 | 5 | 5 | 6 | 6 | 6 |
| 5 | 5 | 5 | 5 | 6 | 6 | 6 |
| 6 | 5 | 5 | 4 | 5 | 5 | 6 |
| 7 | 4 | 4 | 4 | 5 | 5 | 5 |
| 8 | 4 | 4 | 4 | 5 | 5 | 3 |
| 9 | 4 | 3 | 3 | 5 | 4 | |
| 10 | 3 | | | 4 | 4 | |
| 11 | | | | 3 | 4 | |
| 12 | | | | | 3 | |

TABLE VI

| | Anneal Temp. 140° C. Example | | | | | |
|---|---|---|---|---|---|---|
| Laundry Cycles | 1 | 2 | 3 | 4 | 5 | 6 |
| 0 | 6 | 6 | 6 | 6 | 6 | 7 |
| 1 | 6 | 6 | 6 | 6 | 6 | 7 |
| 2 | 5 | 5 | 6 | 6 | 6 | 6 |
| 3 | 5 | 5 | 6 | 5 | 6 | 6 |
| 4 | 5 | 5 | 4 | 5 | 5 | 6 |
| 5 | 5 | 5 | 3 | 4 | 5 | 6 |
| 6 | 4 | 4 | | 4 | 5 | 5 |
| 7 | 4 | 4 | | 3 | 4 | 5 |
| 8 | 3 | 3 | | | 4 | 4 |
| 9 | | 3 | | | 4 | 3 |
| 10 | | | | | 3 | |
| 11 | | | | | | |
| 12 | | | | | | |

The results of Example 7 in Tables I–VI demonstrate that the fluorinated pyromellitate mixtures of the present invention are highly effective surface modifiers. An oil repellency of 5 after 5 laundry cycles is generally considered an excellent rating. Nylon 6 fibers having the compositions of this invention applied thereto achieved an oil repellency of 5 after 5 laundry cycles in 28 out of 33 tests. The temperature annealing range for these tests was from 70° C. to 140° C. Furthermore, the results in Table III demonstrate that nylon 6 fibers having the compositions of the present invention applied thereto achieve satisfactory oil repellency when said fibers were annealed at low temperature (i.e., 90° C.), whereas the results of the comparative example at 90° C. were wholly unsatisfactory. Low temperature annealing is a desirable feature in a commercial operation that applies surfactants to fibers.

In order to evaluate the performance of the fluorinated pyromellitate surfactants of this invention on a polyester fabric, the product of Example 3 was applied to a poly(ethylene terephthalate) fabric, annealed at 90° C., and tested for oil repellency as in Example 7. An oil repellency value of 4 after 7 laundry cycles were obtained. Therefore, the products produced by the process of this invention impart desirable oil repellency properties to polyester fabrics as well as polyamide fabrics.

I claim:

1. A process for the production of an organic fluorinated pyromellitate-containing mixture useful as a fiber surface modifying agent wherein said process comprises:

(a) reacting pyromellitic dianhydride with fluorinated alcohol at a mole ratio of about two moles of fluorinated alcohol per mole of pyromellitic dianhydride to produce a pyromellitate having two fluorinated ester moieties and two carboxylic acid moieties; and (b) reacting said pyromellitate of step (a) with an excess of an oxirane compound selected from the group consisting of epichlorohydrin, epibromohydrin and propylene oxide in the presence of trimellitic anhydride to produce said organic fluorinated pyromellitate-containing mixture.

2. A process according to claim 1 wherein said trimellitic anhydride is added to a reaction medium in step (b) when about 50% to about 100% of the carboxylic acid moieties of said pyromellitate have been esterified.

3. A process according to claim 2 wherein said trimellitic anhydride is added to a reaction medium in said step (b) when about 85% to about 100% of the carboxylic acid moieties of said pyromellitate have been esterified.

4. The process of claim 1 wherein fluorinated alcohol is of the formula: $CF_3(CF_2)_pR'OH$ wherein R' is alkylene of 2 to 6 carbons and p is an integer of 3 to 15.

5. The process of claim 4 wherein said fluorinated alcohol is a mixture of compounds of the formula: $CF_3CF_2(CF_2CF_2)_nCH_2CH_2OH$ with n being from 1 to 6.

6. The process of claim 5 wherein n is from 2 to 5.

7. The process of claim 3 wherein said fluorinated alcohol is of the formula: $CF_3(CF_2)_pR'OH$ wherein R' is alkylene of 2 to 6 carbons and p is an integer of 3 to 15.

8. The process of claim 7 wherein said fluorinated alcohol is a mixture of compounds of the formula:

$CF_3CF_2(CF_2CF_2)_nCH_2CH_2OH$ with n being from 1 to 6.

9. The process of claim 8 wherein n is from 2 to 5.

10. A process according to claim 1 wherein the mole ratio of pyromellitic dianhydride to trimellitic anhydride that is employed ranges from about 10:1 to about 1:3.

11. A process according to claim 10 wherein the mole ratio of pyromellitic dianhydride to trimellitic anhydride that is employed ranges from about 5:1 to about 1:2.

12. A process according to claim 4 wherein the mole ratio of pyromellitic dianhydride to trimellitic anhydride that is employed ranges from about 10:1 to about 1:3.

13. A process according to claim 12 wherein the mole ratio of pyromellitic dianhydride to trimellitic anhydride that is employed ranges from about 5:1 to about 1:2.

14. A process according to claim 3 wherein said step (b) is conducted at a temperature between about 20° C. and about 100° C.

15. A process according to claim 14 wherein said temperature is between about 55° C. and about 75° C.

16. The process of claim 1 wherein said oxirane compound is epichlorohydrin.

17. The process of claim 3 wherein said oxirane compound is epichlorohydrin.

18. The process of claim 4 wherein said oxirane compound is epichlorohydrin.

* * * * *